United States Patent
Dadd et al.

(10) Patent No.: US 9,694,174 B2
(45) Date of Patent: Jul. 4, 2017

(54) MANUFACTURING AN ELECTRODE ARRAY FOR A STIMULATING MEDICAL DEVICE

(71) Applicant: Cochlear Limited, Macquarie University, NSW (AU)

(72) Inventors: Fysh Dadd, Lane Cove (AU); Andy Ho, Tsuen Wan (HK); Shahram Manouchehri, Auburn (AU); Nicholas Charles Kendall Pawsey, North Ryde (AU); Peter Schuller, Turramurra (AU); Peter Raymond Sibary, Luddenham (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 14/622,130

(22) Filed: Feb. 13, 2015

(65) Prior Publication Data

US 2015/0151112 A1 Jun. 4, 2015

Related U.S. Application Data

(60) Division of application No. 12/743,369, filed as application No. PCT/US2008/083794 on Nov. 17, (Continued)

(30) Foreign Application Priority Data

| Dec. 8, 2003 | (AU) | 2003906787 |
| Sep. 16, 2004 | (AU) | 2004905355 |
| Nov. 16, 2007 | (AU) | 2007906282 |

(51) Int. Cl.
*A61N 1/05* (2006.01)
*H01R 43/02* (2006.01)

(52) U.S. Cl.
CPC .......... *A61N 1/0541* (2013.01); *H01R 43/02* (2013.01); *Y10T 29/49002* (2015.01);
(Continued)

(58) Field of Classification Search
CPC .......... H02K 15/0031; H02K 15/0428; H02K 15/04; H02K 15/0435; Y10T 29/49009
See application file for complete search history.

(56) References Cited

U.S. PATENT DOCUMENTS

| 4,602,637 A | 7/1986 | Elmqvist et al. |
| 5,702,438 A | 12/1997 | Avitall |

(Continued)

FOREIGN PATENT DOCUMENTS

| CN | 101970041 A | 2/2011 |
| EP | 1449561 A1 | 8/2004 |

(Continued)

OTHER PUBLICATIONS

International Search Report, International Application No. PCT/US2008/083794, mailed Jan. 22, 2009.
(Continued)

*Primary Examiner* — Minh Trinh
(74) *Attorney, Agent, or Firm* — Hauptman Ham, LLP

(57) ABSTRACT

A method of forming an electrode array is disclosed, the method comprising: forming an elongate comb structure comprising a plurality of longitudinally-spaced electrode contacts extending from and supported by a spine; electrically connecting each of a plurality of electrically conductive pathways to a respective one of the plurality of electrode contacts; placing the conductive pathways adjacent the contacts; placing silicone over the conductive pathways and contacts; curing the silicone so as to substantially retain the longitudinal spacing between neighboring contacts; and severing the spine from the plurality of electrode contacts.

25 Claims, 7 Drawing Sheets

Related U.S. Application Data 2008, now Pat. No. 8,955,211, which is a continuation-in-part of application No. 10/581,090, filed as application No. PCT/AU2004/001726 on Dec. 8, 2004, now Pat. No. 7,950,134.

(52) U.S. Cl.
CPC ...... *Y10T 29/49005* (2015.01); *Y10T 29/4921* (2015.01); *Y10T 29/49204* (2015.01); *Y10T 29/49208* (2015.01); *Y10T 29/49211* (2015.01)

(56) References Cited

U.S. PATENT DOCUMENTS

| | | | |
|---|---|---|---|
| 5,967,841 | A | 10/1999 | Bianca et al. |
| 6,119,044 | A | 9/2000 | Kuzma |
| 6,144,883 | A | 11/2000 | Kuzma |
| 6,151,626 | A | 11/2000 | Tims et al. |
| 6,179,659 | B1 | 1/2001 | Moden |
| 6,306,168 | B1 | 10/2001 | Berrang et al. |
| 6,421,569 | B1 | 7/2002 | Treaba et al. |
| 7,070,631 | B2 | 7/2006 | Monden et al. |
| 7,085,605 | B2 | 8/2006 | Bluger et al. |
| 7,184,843 | B1 | 2/2007 | Cohen |
| 7,240,416 | B2 | 7/2007 | Milojevic et al. |
| 7,837,185 | B2 | 11/2010 | Naito et al. |
| 7,950,134 | B2 * | 5/2011 | Ho .................... H01Q 1/36 29/592.1 |
| 8,955,211 | B2 * | 2/2015 | Dadd .................. A61N 1/0541 29/592.1 |
| 2001/0031909 | A1 | 10/2001 | Faltys et al. |
| 2003/0088301 | A1 | 5/2003 | King |
| 2003/0097165 | A1 | 5/2003 | Krulevitch et al. |
| 2006/0074460 | A1 | 4/2006 | Maghribi et al. |
| 2006/0085055 | A1 | 4/2006 | Dadd et al. |
| 2007/0088335 | A1 | 4/2007 | Jolly |
| 2007/0128940 | A1 | 6/2007 | Ho et al. |
| 2007/0225776 | A1 | 9/2007 | Fritsch et al. |
| 2011/0016710 | A1 | 1/2011 | Dadd et al. |

FOREIGN PATENT DOCUMENTS

| | | |
|---|---|---|
| WO | 00/71063 A1 | 11/2000 |
| WO | 02/089907 A1 | 11/2002 |
| WO | 2007/050212 A2 | 5/2007 |
| WO | 2009/062266 A1 | 5/2009 |
| WO | 2009/065171 A1 | 5/2009 |

OTHER PUBLICATIONS

International Preliminary Examination Report, International Application No. PCT/US2008/083794, mailed Nov. 10, 2009.
Written Opinion, International Application No. PCT/US2008/083794, mailed Jan. 22, 2009.
Extended European Search Report, European Application No. 08850709.0, mailed Feb. 4, 2011 (8 pages).
International Search Report and Written Opinion, International Application No. PCT/AU2008/001893, mailed Mar. 23, 2009 (6 pages).
Chinese Office Action for Chinese Application No. 200880122235.0 mailed Jun. 3, 2013 along with an English Translation.

* cited by examiner

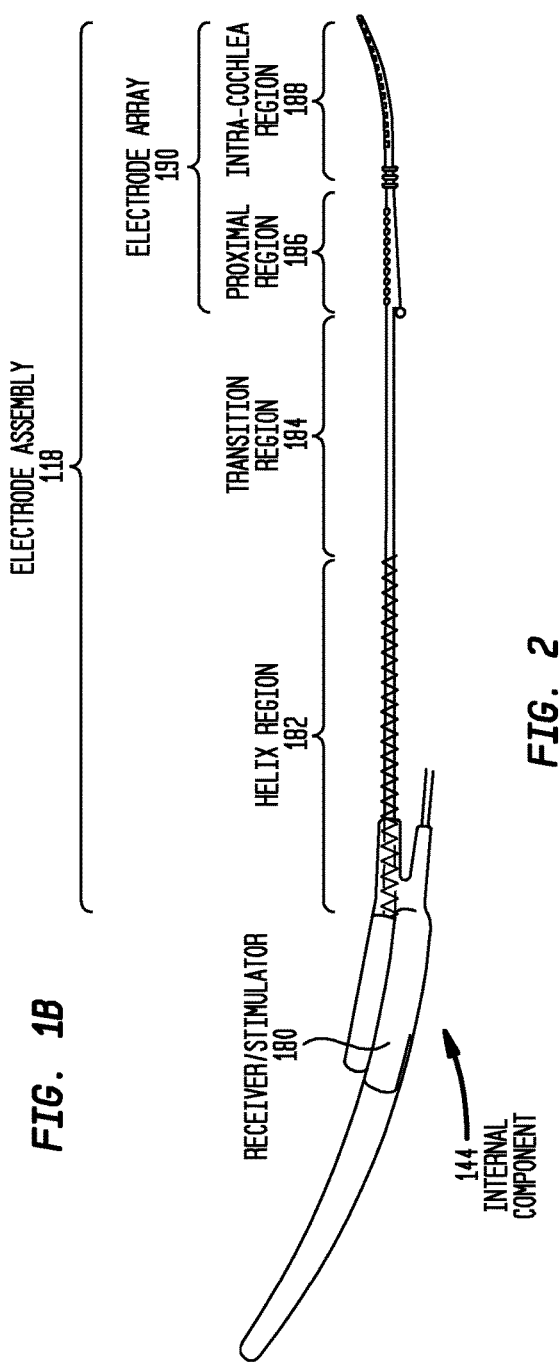
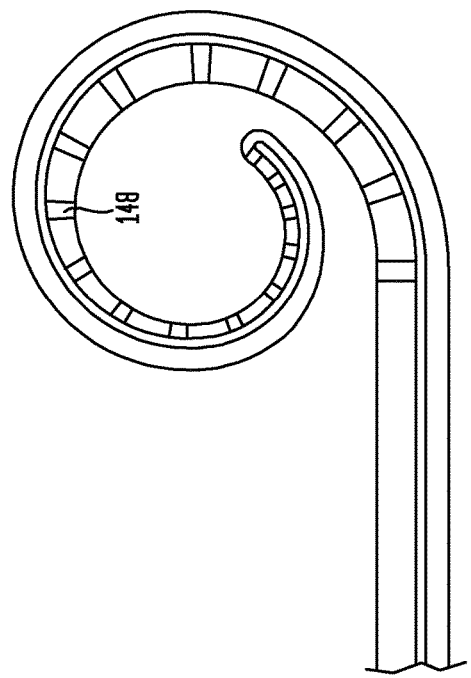
FIG. 1B
FIG. 2

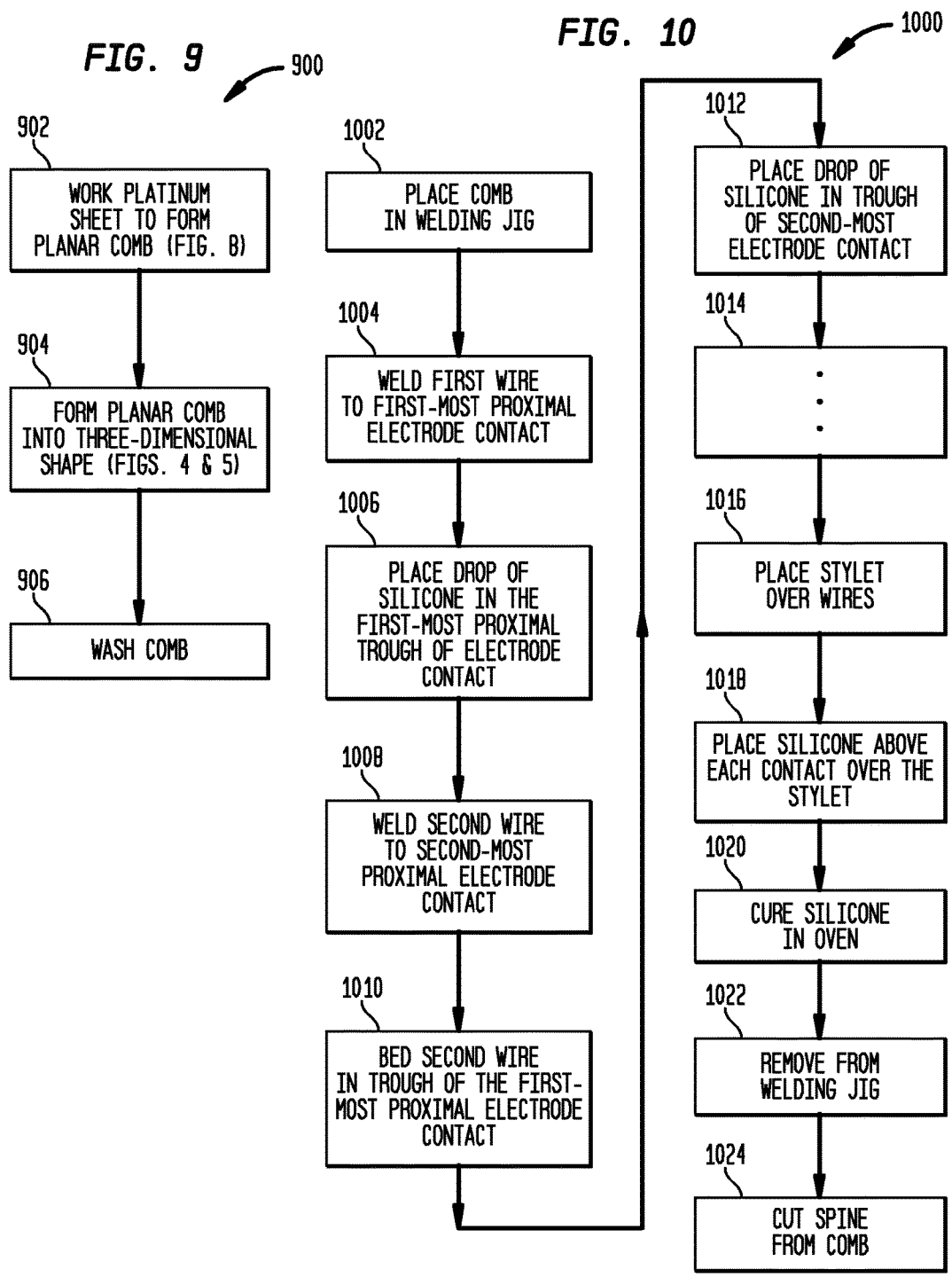

MANUFACTURING AN ELECTRODE ARRAY FOR A STIMULATING MEDICAL DEVICE

CROSS-REFERENCE TO RELATED APPLICATIONS

The present application is a Divisional application of U.S. patent application Ser. No. 12/743,369, filed Aug. 26, 2010, which is a National Stage Application of International Application No. PCT/US2008/083794, filed Nov. 17, 2008, which claims priority from Australian Patent Application No. 2007906282, filed Nov. 16, 2007. In addition, the present application is a Continuation-in-part of U.S. patent application Ser. No. 10/581,090, filed Feb. 16, 2007, which is a National Stage Application of International Application No. PCT/AU2004/01726, filed Dec. 8, 2004, which claims priority from Australian Patent Application No. 2004905355, filed on Sep. 16, 2004 and Australian Patent Application No. 2003906787, filed on Dec. 8, 2003. All of the applications mentioned above, are hereby incorporated by reference herein in their entirety.

BACKGROUND

The present invention relates generally to implantable electrodes, and more particularly, to an electrode array for use in medical implants.

RELATED ART

There are a variety of medical implants that deliver electrical stimulation to a patient or recipient ("recipient" herein) for a variety of therapeutic benefits. For example, the hair cells of the cochlea of a normal healthy ear convert acoustic signals into nerve impulses. People who are profoundly deaf due to the absence or destruction of cochlea hair cells are unable to derive suitable benefit from conventional hearing aid devices. A type of prosthetic hearing implant system commonly referred to as a cochlear implant has been developed to provide such persons with the ability to perceive sound. A cochlear implant bypasses the hair cells in the cochlea to directly deliver electrical stimulation to auditory nerve fibers, thereby allowing the brain to perceive a hearing sensation resembling the natural hearing sensation.

The electrodes utilized in stimulating medical implants vary according to the device and tissue which is to be stimulated. For example, the cochlea is tonotopically mapped and partitioned into regions, with each region being responsive to stimulus signals in a particular frequency range. To accommodate this property of the cochlea, cochlear implants typically include an array of electrodes each constructed and arranged to deliver an appropriate stimulating signal to a particular region of the cochlea.

SUMMARY

In accordance with one embodiment of the present invention, a method of forming an electrode array is disclosed, the method comprising: forming an elongate comb structure comprising a plurality of longitudinally-spaced electrode contacts extending from and supported by a spine; electrically connecting a plurality of electrically conductive pathways to the plurality of electrode contacts; constraining the plurality of contacts to substantially retain the longitudinal spacing between neighboring contacts; and severing the electrode contacts from the spine.

In accordance with another embodiment of the present invention, a method of forming an electrode array is disclosed, the method comprising: forming an elongate comb structure comprising a plurality of longitudinally-spaced electrode contacts extending from and supported by a spine; electrically connecting each of a plurality of electrically conductive pathways to a respective one of the plurality of electrode contacts; placing the conductive pathways adjacent the contacts; placing silicone over the conductive pathways and contacts; curing the silicone so as to substantially retain the longitudinal spacing between neighboring contacts; and severing the spine from the plurality of electrode contacts.

BRIEF DESCRIPTION OF THE DRAWINGS

Aspects and embodiments of the present invention are described herein with reference to the accompanying drawings, in which:

FIG. 1B is a side view of the implantable components of the cochlear implant illustrated in FIG. 1A;

FIG. 2 is a side view of an embodiment of the electrode array illustrated in FIGS. 1A and 1B in a curled orientation;

FIG. 9 is a flowchart of a method of making the comb of FIG. 4, in accordance with embodiments of the present invention;

FIG. 10 is a flowchart of a method of making an electrode assembly shown in FIGS. 1-3, using the comb of FIG. 4, in accordance with embodiments of the present invention;

DETAILED DESCRIPTION

Embodiments of the present invention are described herein primarily in connection with one type of hearing prosthesis, namely a cochlear implant. Cochlear implants generally refer to hearing prostheses that deliver electrical stimulation to the cochlea of a recipient. As used herein, the term "cochlear implant" also include hearing prostheses that deliver electrical stimulation in combination with other types of stimulation, such as acoustic or mechanical stimulation. It would be appreciated that embodiments of the present invention may be implemented in any cochlear implant or other hearing prosthesis now known or later developed, including auditory brain stimulators, or implantable hearing prostheses that also acoustically or mechanically stimulate components of the recipient's middle or inner ear.

Figure 1A:
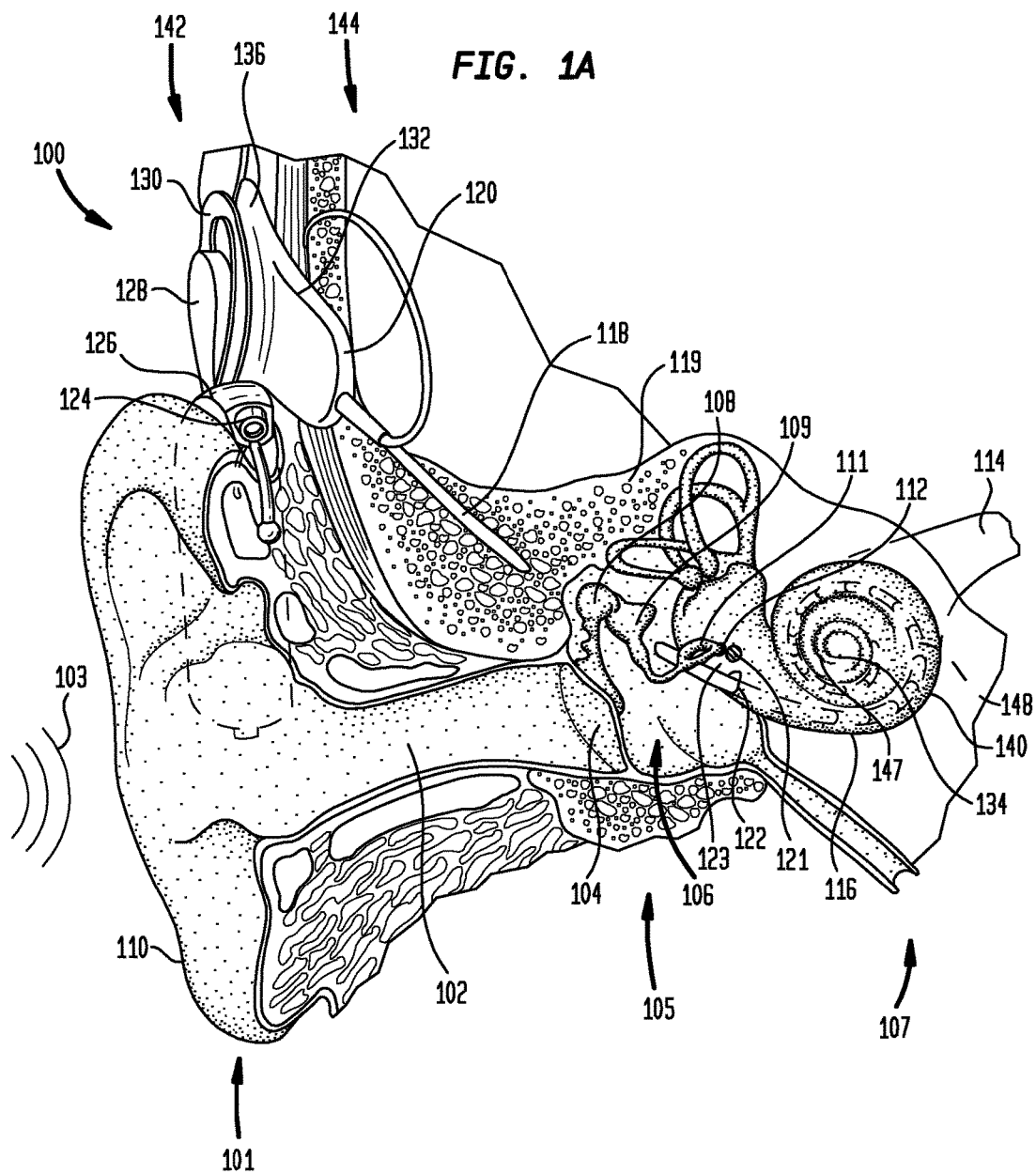
FIG. 1A is a perspective view of an exemplary medical device, a cochlear implant, having an electrode assembly which may be advantageously manufactured using embodiments of the present invention.

FIG. 1A is a perspective view of an exemplary medical device having an electrode carrier member manufactured in accordance with the teachings of the present invention. Specifically, FIG. 1A is perspective view of a cochlear implant 100 implanted in a recipient having an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124, for detecting sound, a sound processing unit 126, a power source (not shown), and an external transmitter unit 128. External transmitter unit 128 comprises an external coil 130 and, preferably, a magnet (not shown) fixed relative to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown).

Internal component 144 comprises an internal receiver unit 132, a stimulator unit 120, and an elongate electrode assembly 118, also referred to as a lead. Internal receiver unit 132 comprises an internal coil 136, and preferably, a magnet (also not shown) fixed relative to the internal coil. Internal receiver unit 132 and stimulator unit 120 are hermetically sealed within a biocompatible housing, and are sometimes collectively referred to as a stimulator/receiver unit. The internal coil receives power and stimulation data from external coil 130, as noted above. Elongate electrode assembly 118 has a proximal end connected to stimulator unit 120, and a distal end implanted in cochlea 140. Electrode assembly 118 extends from stimulator unit 120 to cochlea 140 through mastoid bone 119. As described below, electrode assembly 118 is implanted in cochlea 140. In some embodiments electrode assembly 118 may be implanted at least in basal region 116, and sometimes further. For example, electrode assembly 118 may extend towards apical region, or apex, 134 of cochlea 140. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a plurality of longitudinally aligned and distally extending electrodes 148 disposed along a length thereof. In most practical applications, electrodes 148 are integrated into electrode assembly 118. As such, electrodes 148 are referred to herein as being disposed in electrode assembly 118. Stimulator unit 120 generates stimulation signals which are applied by electrodes 148 to cochlea 140, thereby stimulating auditory nerve 114.

In cochlear implant 100, external coil 130 transmits electrical signals (i.e., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding. In use, implantable receiver unit 132 may be positioned in a recess of the temporal bone adjacent auricle 110 of the recipient.

While various aspects of the present invention are described with reference to a cochlear implant, it will be understood that various aspects of the present invention are equally applicable to other stimulating medical devices having an array of electrical simulating electrodes such as auditory brain implant (ABI), functional electrical stimulation (FES), spinal cord stimulation (SCS), penetrating ABI electrodes (PABI), and so on. Further, it should be appreciated that the present invention is applicable to stimulating medical devices having electrical stimulating electrodes of all types such as straight electrodes, peri-modiolar electrodes and short/basilar electrodes.

Throughout this description, the term "electrode array" means a collection of two or more electrodes, sometimes referred to as electrode contacts or simply contacts herein. The term "electrode array" also refers to or includes the portion of the carrier member in which the electrodes are disposed. It should be appreciated that in the literature and prior art the term "electrode array" refers to both, the electrodes as well as the combination of electrodes and the carrier member in which the electrodes are disposed.

FIG. 1B is a side view of an internal component 144 of a conventional cochlear implant. Internal component 144 comprises a receiver/stimulator 180 and an electrode assembly or lead 118. Electrode assembly 118 includes a helix region 182, a transition region 184, a proximal region 186, and an intra-cochlear region 188. Proximal region 186 and intra-cochlear region 188 form an electrode array 190. Electrode array 190, and in particular, intra-cochlear region 188 of electrode array 190, supports a plurality of electrode contacts 149. These electrode contacts 148 are each connected to a respective conductive pathway, such as wires, PCB traces, etc. (not shown) which are connected through lead 118 to receiver/stimulator 180, through which respective stimulating electrical signals for each electrode contact 148 travel.

Figure 3:
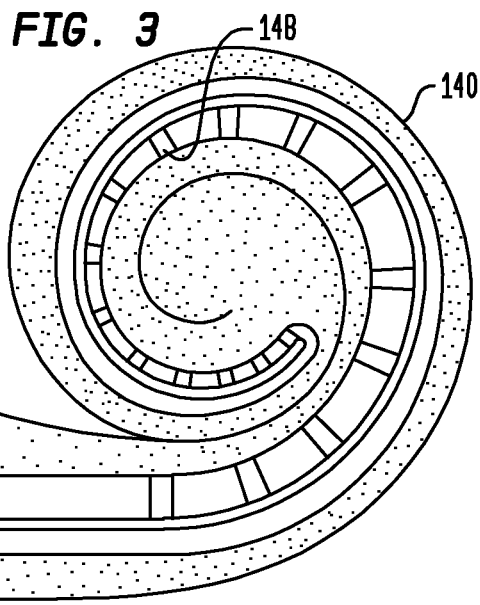
FIG. 3 is a schematic view of the electrode array of FIG. 2 in situ in a cochlea.

FIG. 2 is a side view of electrode array 190 in a curled orientation, as it would be when in situ in a patient's cochlea, with electrode contacts 148 located on the inside of the curve. FIG. 3 shows the electrode array of FIG. 2 in situ in a patient's cochlea 140. In this exemplary application, electrode contacts 148 are shown in electrical contact with the tissue to be stimulated, as will be understood by those skilled in the art.

Figure 4:
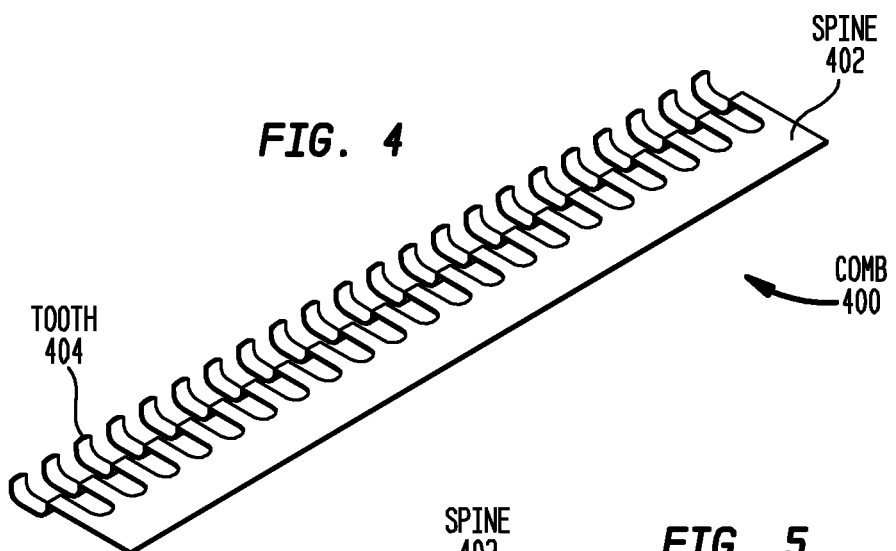
FIG. 4 is a perspective view of intermediate manufacturing product, a comb, which may be used during manufacture of an electrode array in accordance with embodiments of the present invention.

FIG. 4 is a perspective view of an intermediate product 400 made during manufacture of an electrode array 190 in accordance with embodiments of the present invention. As shown in FIG. 4, electrode contacts 148 are formed from the unitary piece 400 of electrically conductive material, referred to herein as a "comb" 400. Comb 400 includes a number of teeth 404 extending from and supported by a spine 402. In the example shown, there are twenty-two teeth/electrode contacts 404 extending from an elongate spine 402. In practice, there may be any number of electrode contacts, ranging from 2 to 256 electrode contacts, or more. This may, for example, include 3, 4, 5, 6, 7, 8, 9, 10, 10-20, 20-30, 30-50, 50-100, 100-150, 150-200, 200-256, 256-300 electrode contacts, etc.

Electrode contacts 148 are preferably made from platinum, but any other suitable material such as iridium, a platinum/iridium alloy, or other platinum or iridium alloy may be used, as will be understood by one of ordinary skill in the art.

Figure 5:
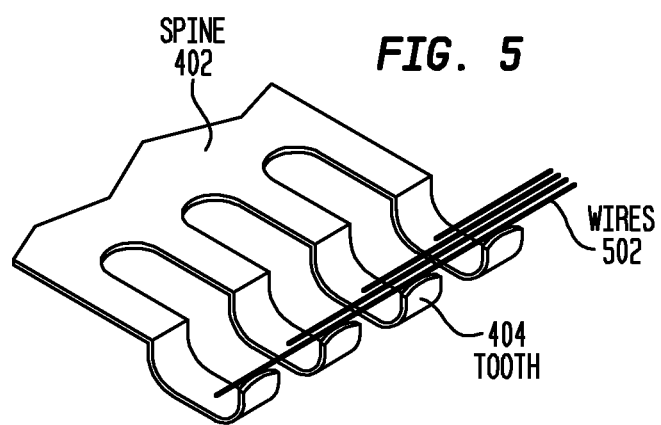
FIG. 5 is a perspective magnified view of a portion of the comb illustrated in FIG. 4.
Figure 6:
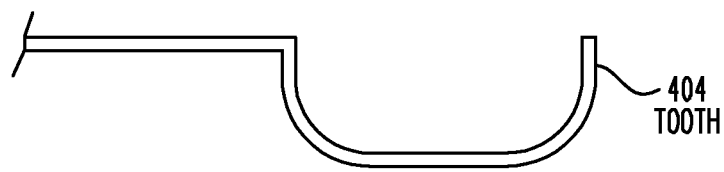
FIG. 6 is a side view of an individual electrode contact on the comb illustrated in FIG. 5, in accordance with embodiments of the present invention.

For certain applications, electrode contacts 148 are preferably formed in a U-shape, as shown in FIGS. 5 and 6. FIG. 5 is a magnified view of a portion of comb 400; FIG. 6 is a side view of an individual electrode contact 148 on comb 400. At this stage of manufacture, electrodes 148 are in the form of teeth of comb 400. As shown in FIG. 6, teeth 404 have a relatively large exposed surface area. Electrode array 190 is particularly adapted to bend and flex in one direction, making it well-suited to inserting into a curved body cavity, such as cochlea 50.

Preferably, the width of each tooth 404 of comb 400 is 0.3 mm and the gap between them is approximately 0.3 mm. The total length of such a comb is approximately 13 mm, based upon the preferred number of teeth 404. Of course, these dimensions may be varied as required by the particular design and application.

Figure 7:
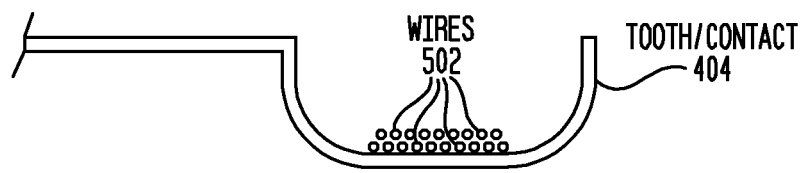
FIG. 7 is a side view of the electrode contact illustrated in FIG. 6 with conductive pathways in the form of wires shown positioned in the trough of the contact.
Figure 8:
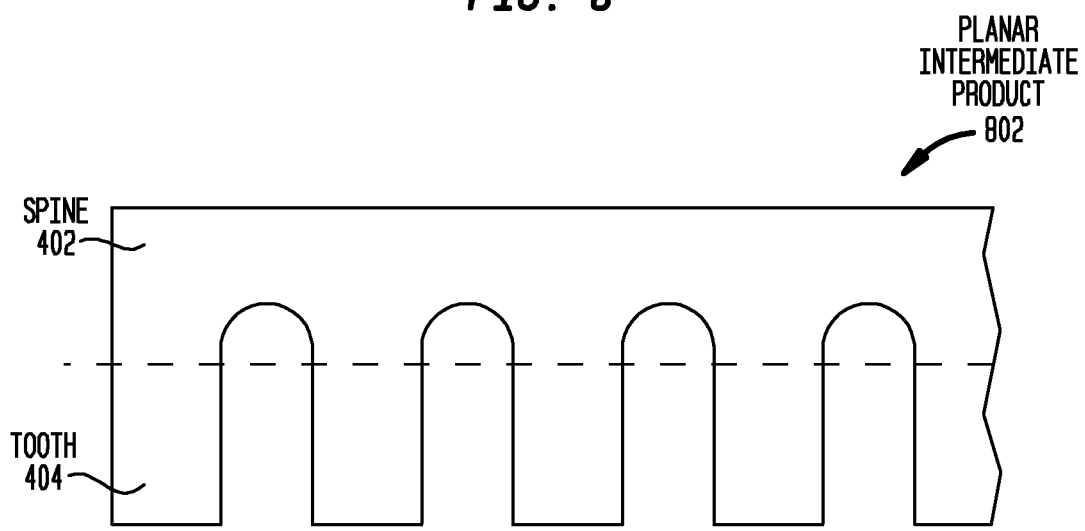
FIG. 8 is a top view of an intermediate manufactured product showing a cut line for removing the spine from the teeth of the comb, in accordance with embodiments of the present invention.

FIG. 5 also shows conductive pathways (in this example wires) 502 connected to respective teeth 404. The method of connection may be done in any suitable manner such as welding, as will be described in more detail below. FIG. 7 is a side view of a tooth/contact 148 showing the collection of conductive wires 502 being supported in the trough of one of the U-shaped teeth 404. Once wires 502 have been connected to electrode contacts 148, electrode contacts 148 are cut off or otherwise severed from spine 402. The cut point is preferably just below spine 402 so that contacts 148 are of a substantially rectangular shape, as shown in FIG. 8.

Spine 402 of comb 400 serves a dual function. Firstly, spine 402 connects electrode contacts 148 so that the contacts are in one piece and thus in a fixed location relative to each other. Secondly, spine 402 provides a secure holding point to secure comb 400 to the welding jig (not shown), thus holding electrode contacts 3 during subsequent processing operations.

A method of forming the comb 400 is described below with reference to FIG. 9. At step 902, a platinum sheet having a thickness of, for example, 50 um, is worked (in this example, punched) to provide the shape of comb 400 as shown in FIG. 8. Of course other methods may be used to form comb 400, such as EDM to micromachine the combs. It is envisaged that in certain applications smaller contacts will be desired and once the limitations of punching electrodes has been reached they could be cut out using a laser and subsequently formed using the methods described above or out using a laser and formed using laser ablation.

Rotary knife tooling could also be used to cut a platinum sheet, or other materials, into electrode contacts with a spine or with an adhesive backing where the rotary blades cut through the first layer leaving the spine intact, and following forming, welding, molding etc. the second layer can be peeled off. Various other techniques for punching, cutting, and otherwise working the sheet are also described in International Patent Publication No. WO 02/089907.

In step 904, the planar comb is formed into its 3-dimensional shape as shown in FIGS. 4 and 5 by forming a U-shape in teeth 804. In step 906, the shaped comb is washed in preparation for welding. It is possible to form a plurality of combs from a single sheet of material. For example, about 25 combs can be formed quasi-simultaneously from a platinum strip 500 mm in length via a pneumatic press.

The method of forming electrodes 148 from the formed comb 400 is described with reference to FIG. 10. At step 1002, the finished three-dimensional comb 400 is placed into a welding jig (not shown) ready for wires 32 to be joined to the comb. The comb 400 is secured by being held along the length of the spine 31, thereby providing a secure hold.

At step 1004, a wire 32 is welded to the most proximal electrode contact 148. At step 1006, an amount (for example a droplet) of silicone is placed in the trough of the electrode contact 148. In step 1008, a second wire 502 is welded to the second most proximal electrode contact 148. At step 1010, the wire from the second contact is bedded down into the silicone droplet in the trough of the first electrode. In step 1012, a droplet of silicone is placed in the trough of the second electrode contact. In step 1014, steps 1002 through 1012 are repeated until all wires 502 have been connected to their respective electrode contacts 148. As one of ordinary skill in the art would appreciate, the sequence of placing the wires and silicone may be different in alternative embodiments of the present invention. Similarly, it should be appreciated that each wire, or all wires, may be placed in the electrode troughs in a single operation followed by the application of silicone to none, some or all of such troughs.

After all wires have been connected, a production stylet (for example, a PTFE coated wire) is suspended above or otherwise placed on top of the wires in step 1016. This stylet is removed later and forms the lumen of lead. In step 608, silicone is placed above each contact over the production stylet, to form a sub-assembly, and the silicone is cured in an oven in step 1020. At this point in the process the electrode contacts 148 are substantially constrained in a relative longitudinal position thereby substantially retaining the longitudinal spacing between neighboring contacts.

Figure 11:
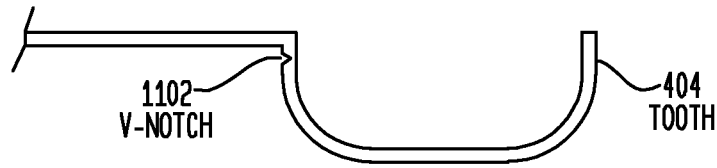
FIG. 11 shows an alternative electrode contact configuration with a V-notch.
Figure 12:
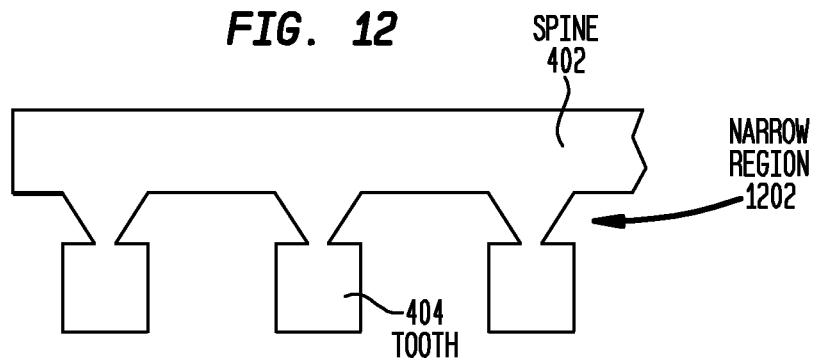
FIG. 12 shows an alternative configuration for the comb illustrated in FIGS. 4 and 5.

In step 1022, the sub-assembly is removed from the welding jig. In step 1024, spine 402 is then severed such as by cutting from comb 400 to leave the individual electrode contacts 148. In alternative embodiments, a V-notch 1102 is formed in teeth 148 to facilitate separation of the teeth from spine 402 simply by "snapping off" the teeth, as shown in FIG. 11. Alternatively, the separation of teeth 804 from spine 402 may be facilitated by forming a part of the teeth 804 with a narrower part such as shown in FIG. 12. This provides an alternative "snapping" option.

It is also possible to change the order of some of the steps above. For example, the step 501 of forming the comb into a 3-dimensional shape may be performed after the steps of welding the conductive wires 32 into place. Performing the steps in other sequences is also contemplated. It is also possible to connect 2 or more wires to one or more electrodes. This may provide an advantage of redundancy and may increase the robustness of the resulting lead 20.

The process continues as is known in the art. In particular, one method of molding of electrode array is as described in U.S. Pat. No. 6,421,569, the disclosure of which is incorporated by reference.

The sub-assembly is preferably carefully curved to match the shape of a curved molding die (not shown). The assembly is then placed in the curved molding die with the contacts being located closer to the medial side (inside of the curve). The space in the die is packed with silicone material. A matching die cover is placed over the assembly and pressed down. The die is then placed in an oven to cure the silicone. The die is then open to allow the resulting electrode array to be removed from the die.

The electrode array described above forms the distal end of lead assembly 20 that is adapted to be connected to implantable receiver/stimulator 10 (FIG. 1). Receiver/stimulator 10 is typically housed within a metallic case. In one application, receiver/stimulator 10 has an array of feed through terminals corresponding to its multiple channels.

The electrode array facilitates the use of non-flat surface finishes. For example, dimpled, corrugated, pitted or irregular geometric shapes may be provided on the surface of electrode contacts 30. These varied surface finishes may be achieved by stamping a pattern finish in the punching and pre-forming operation. Alternatively, the contact areas may be roughened by controlled sandblasting of the array before or after molding. Surface modification may also be achieved using laser ablation via the direct write method or using a mask at almost any stage during the manufacture of the electrode. A non-flat surface area may have the advantage of increasing the effective size of the electrode contact without requiring a larger electrode contact. This allows smaller electrode contacts with equivalent surface areas to be utilized. Various methods of creating such surface finishes are described in for example, U.S. Pat. No. 4,602,637 and PCT Application No. PCT/US2006/036966 (WO2007/050212)

Alternatively, the electrode contacts may be substantially planar rather than U-shaped as described above. In this embodiment, comb 400 may be punched rather than formed. Such embodiments provide for a relatively simpler manufacturing processing. In alternative embodiments, electrode contacts 30 have a shape other than rectangular, such as square, circular, triangular or oval.

In yet another alternative, the various aspects of the present invention may be used to provide electrode arrays with a variable pitch. Such constructions are disclosed in U.S. Pat. No. 7,184,843. For example, comb 400 can be formed with teeth 404 having a variable spacing, with the distal electrode contacts lying closer together than the proximal ones. Other variations on the spacing between electrode contacts may also be utilized.

Figure 13:
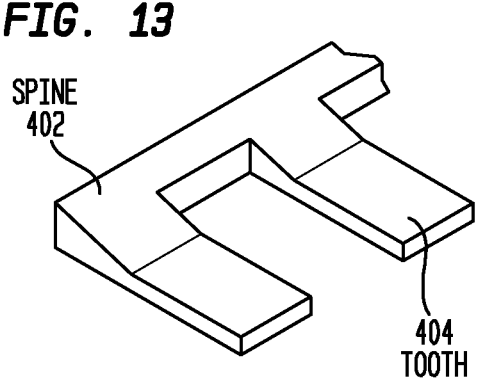
FIG. 13 shows an alternative configuration for the comb illustrated in FIGS. 4 and 5.

In yet another alternative, a stepped sheet of a varying thickness can be used to create comb 400 with spine 402, as shown in FIG. 13. This has the advantage of increasing the torsional stability of teeth/electrode contacts 404 while maintaining a relatively consistent contact thickness.

Figure 14:
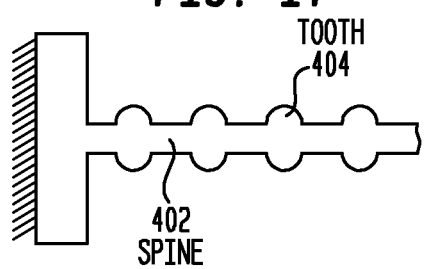
FIG. 14 shows an alternative configuration for the comb illustrated in FIGS. 4 and 5.

In yet another alternative, spine 402 runs between electrode contacts 404, as shown in FIG. 14.

Figure 15:
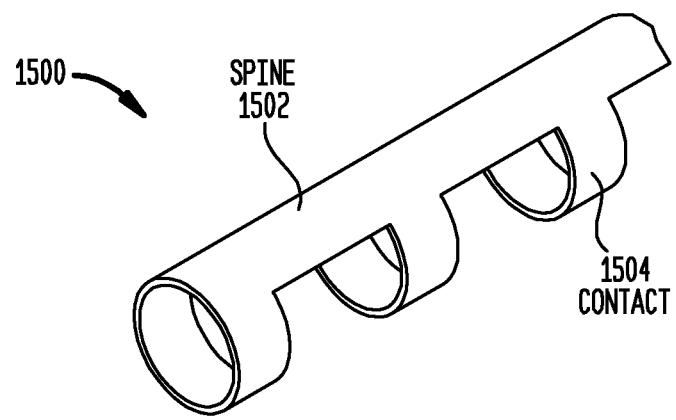
FIG. 15 shows an alternative configuration for the comb illustrated in FIGS. 4 and 5.

In alternative embodiments, comb 300 may be formed to have a substantially cylindrical shape as shown in FIG. 15. In one such embodiment, electrode contacts 404 are circular with both ends connected to spine 402. In manufacturing such a structure, teeth 404 may be rolled into shape, or alternatively, they may be formed by etching the shape from a continuous platinum tube.

Figure 16:
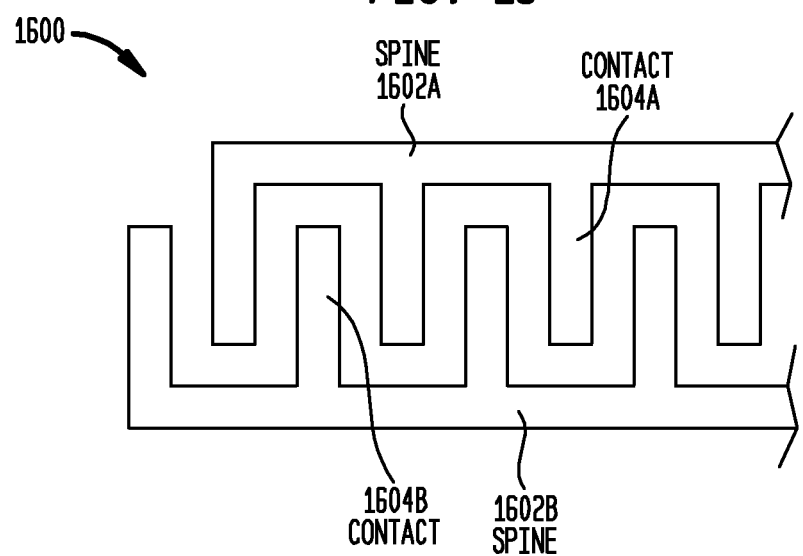
FIG. 16 shows an arrangement of two combs on sheet of electrically conductive material, in accordance with embodiments of the present invention.

In yet another embodiment, two separate (not connected) spines 31, 31' hold two sets of respective electrode contacts 30, 30' as shown in FIG. 16.

In yet another alternative, two or more arrays may be formed and laminated together to form a single tissue stimulating electrode assembly. For example, such an assembly might be formed from a first lamination having seven electrodes, a second lamination having eight electrodes, and a third lamination having eight electrodes, to form an electrode assembly having 23 electrodes. In the case of a cochlear electrode array, the formed array may have 22 intracochlear electrodes and one extracochlear electrode. Such a lamination process would preferably result in a linear array of the 22 electrodes. Other combinations of layers, and other quantities of electrodes in each layer, may be utilized to form arrays of different lengths.

In the descriptions above, the electrically conductive pathways may be provided by any suitable means including wires, conductive deposits, conductive tracks, and the like.

The above and other embodiments of forming electrode arrays, and the electrode arrays themselves, may provide one or more advantages over conventional methods. Such advantages may include, and are not limited to the following: they may be manufactured using easy, low cost technology; they have lower parts count (for 22 electrode contacts, the parts count has reduced by 21); they have higher a Manufacturing Yield Rate (fewer problems during holding contacts during at least welding); and they enable greater accuracy and consistency with contact placement.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A method of forming an electrode array comprising:
    obtaining a structure comprising a plurality of spaced apart electrode contacts supported by a support structure;
    electrically connecting respective electrically conductive pathways to electrode contacts;
    placing a curable material over the conductive pathways and contacts;
    curing the curable material so as to substantially retain the spacing between neighboring contacts; and
    disconnecting the support structure from the plurality of electrode contacts.

2. The method of claim 1, further comprising:
    shaping the electrode contacts into the trough shape,
    wherein electrically connecting the plurality of respective electrically conductive pathways to respective electrode contacts comprises:
    connecting a plurality of respective electrically conductive pathways to respective electrode contacts in the trough of the electrical contacts.

3. The method of claim 1, wherein the support structure is the spine, and wherein the spaced apart electrode contacts are longitudinally-spaced.

4. The method of claim 1, wherein obtaining the obtained structure comprises forming the obtained structure.

5. The method of claim 1, wherein the obtained structure is an elongate comb.

6. The method of claim 1, further comprising the action of placing the conductive pathways adjacent the contacts.

7. The method of claim 1, wherein at least one of:
(i) the support structure is a spine, and wherein the spaced apparatus electrode contacts are longitudinally-spaced; or
(ii) the method further comprises:
shaping the electrode contacts into a trough shape, wherein electrically connecting the plurality of respective electrically conductive pathways to respective electrode contacts comprises:
connecting a plurality of respective electrically conductive pathways to respective electrode contacts in the trough of the electrical contacts.

8. The method of claim 1, wherein curing the curable material occurs before disconnecting the support structure.

9. A method of forming an electrode array comprising:
obtaining an apparatus comprising a plurality of spaced apart electrode contacts supported by a support structure;
electrically connecting respective electrically conductive pathways to respective electrode contacts of the plurality of contacts;
after obtaining the apparatus, constraining the plurality of electrode contacts to substantially retain the spacing between the contacts; and
removing the support structure from the plurality of electrode contacts.

10. The method of claim 9, wherein the action of obtaining the apparatus comprises forming the apparatus.

11. The method of claim 9, wherein the apparatus is an elongate comb structure.

12. The method of claim 9, wherein the apparatus comprises a spine supporting the plurality of electrode contacts.

13. The method of claim 9, wherein the apparatus is a monolithic component.

14. The method of claim 9, wherein the action of connecting the respective electrically conductive pathways to the respective electrode contacts comprises:
welding respective electrically conductive pathways to respective electrode contacts.

15. The method of claim 9, wherein:
at least one of the plurality of electrode contacts has a trough; and
connecting the electrically conductive pathways to the electrode contacts comprises:
retaining the plurality of conductive pathways in the trough.

16. The method of claim 15, wherein retaining the plurality of conductive pathways in the trough comprises:
placing a droplet of silicone into the trough; and
placing the plurality of conductive pathways in the trough of the at least one electrode contact.

17. The method of claim 9, wherein obtaining the apparatus comprises:
forming an elongate comb structure by forming a comb from a sheet of biocompatible and electrically conductive material.

18. The method of claim 17, further comprising:
shaping each of the plurality of electrode contacts into a trough shape, wherein connecting respective electrically conductive pathways to respective electrode contacts comprises:
connecting respective electrically conductive pathways to respective troughs of the respective electrode contacts.

19. The method of claim 9, wherein:
obtaining the apparatus comprises forming the apparatus;
the formed apparatus is an elongate comb structure;
the support structure is a spine;
the electrode contacts are longitudinally-spaced and extend from the spine;
constraining the plurality of electrode contacts substantially retains the longitudinal spacing between neighboring contacts; and
removing the support structure from the plurality of electrode contacts comprises detaching the spine from the plurality of electrode contacts.

20. The method of claim 9, wherein at least one of:
the apparatus is an elongate comb structure;
the apparatus is a monolithic component;
the apparatus comprises a spine supporting the plurality of electrode contacts; or
the method further includes forming an elongate comb structure by forming a comb from a sheet of biocompatible and electrically conductive material.

21. The method of claim 9, wherein removing the support structure from the plurality of electrodes is executed after constraining the plurality of electrode contacts, and wherein the obtained apparatus is such that the plurality of spaced apparatus electrode contacts are constrained to substantially retain the spacing between the contacts prior to electrically connecting respective electrically conductive pathways to respective electrode contacts.

22. The method of claim 9, further comprising placing the apparatus supported by a support structure in a mold, wherein the mold is separate from the support structure.

23. The method of claim 9, wherein constraining the plurality of electrode contacts occurs before removing the support structure from the plurality of electrode contacts.

24. The method of claim 23, wherein the obtained apparatus is a monolithic component comprising the support structure and the electrode contacts.

25. A method of forming an electrode array comprising:
obtaining an apparatus comprising a plurality of spaced apart electrode contacts supported by a support structure;
electrically connecting respective electrically conductive pathways to electrode contacts;
placing a curable material over the conductive pathways and contacts;
curing the curable material so as to substantially retain the spacing between neighboring contacts; and
disconnecting the support structure from the plurality of electrode contacts,
wherein the method further comprises placing the apparatus comprising the plurality of spaced apart electrode contacts supported by the support structure into a mold separate from the support structure prior to placing the curable material over the conductive pathways and contacts.

* * * * *